(12) United States Patent
Chen

(10) Patent No.: US 7,259,871 B2
(45) Date of Patent: Aug. 21, 2007

(54) APPARATUS AND METHOD FOR RAPID AND PRECISE SCANNING OF THREE-DIMENSIONAL OCCLUSAL PROFILE OF DENTAL CAST

(75) Inventor: Liang-Chia Chen, Jhonghe (TW)

(73) Assignee: National Taipei University of Technology, Taipei (TW)

( * ) Notice: Subject to any disclaimer, the term of this patent is extended or adjusted under 35 U.S.C. 154(b) by 458 days.

(21) Appl. No.: 10/771,363

(22) Filed: Feb. 5, 2004

(65) Prior Publication Data

US 2004/0252312 A1    Dec. 16, 2004

(30) Foreign Application Priority Data

Jun. 12, 2003   (TW)   ............................... 92116005 A

(51) Int. Cl.
  *G01B 11/24*   (2006.01)
  *G01B 11/30*   (2006.01)
  *G01N 21/86*   (2006.01)
  *G01V 8/00*    (2006.01)
  *G06K 9/00*    (2006.01)

(52) U.S. Cl. ................. 356/603; 356/602; 250/559.22; 250/559.23; 382/154

(58) Field of Classification Search ..................... None
See application file for complete search history.

(56) References Cited

U.S. PATENT DOCUMENTS

| | | | | |
|---|---|---|---|---|
| 5,671,056 A | * | 9/1997 | Sato | ........................... 356/602 |
| 5,760,906 A | * | 6/1998 | Sato | ........................... 356/602 |
| 6,002,423 A | * | 12/1999 | Rappaport et al. | ............ 348/42 |
| 6,263,234 B1 | | 7/2001 | Engelhardt | |
| 6,506,054 B2 | * | 1/2003 | Shoher et al. | .............. 433/223 |
| 6,974,964 B1 | * | 12/2005 | Wang | .................... 250/559.29 |

\* cited by examiner

*Primary Examiner*—Gregory J. Toatley, Jr.
*Assistant Examiner*—Gordon J. Stock, Jr.
(74) *Attorney, Agent, or Firm*—Rabin & Berdo, P.C.

(57) ABSTRACT

This invention relates to an apparatus and a method for rapid and precise scanning of the three-dimensional (3-D) profile of a dental cast. Disclosed is a measurement apparatus comprising two symmetrically arranged optical projection units and plural image capturing units each including optical components and optical lenses. The geometrical relationship between the optical projection units and the plaster dental cast are such arranged to ensure precise projection of laser beams and comprehensive measurement. The plural image capturing units serve to capture the reflected, structured light patterns, based on which patterns a 3-D occlusal profile is rapidly and precisely calculated through the triangulation principle, thereby allowing efficient and precise measurement of the 3-D occlusal profile of the plaster dental cast.

11 Claims, 2 Drawing Sheets

APPARATUS AND METHOD FOR RAPID AND PRECISE SCANNING OF THREE-DIMENSIONAL OCCLUSAL PROFILE OF DENTAL CAST

BACKGROUND OF THE INVENTION

1. Field of Invention

This invention relates to a non-contact, optical apparatus for rapid and precise scanning of the three-dimensional (3-D) occlusal profile of a dental cast, and especially to a non-contact, optical system and method for measuring the 3-D occlusal profile of a dental cast as required by modern crown reconstruction works. According to this invention, a structured light beam (a linear light pattern produced by projecting a semiconductor laser through an optical lens to serve as measuring means) is implemented in a probe body and projected onto an object to be measured at a desired orientation; plural capturing units are implemented to capture comprehensive information representing the 3-D occlusal profile, based on which information the 3-D occlusal profile is calculated through the triangulation principle, thereby allowing efficient and precise measurement of the 3-D occlusal profile of the plaster dental cast.

2. Description of Prior Art

The recent development of tooth restoration works has turned progressed from the conventional tooth mold modeling and precision de-waxing casting techniques onto 3-D occlusal profile measuring technique in cooperation with dental cast reconstructions by computer-aided-design (CAD), as well as dental cast milling by computer-aided-manufacturing (CAM). The manufacture of artificial teeth, in responsive of the current market demands, focuses on the rapid and precise procedure in the hope of minimizing each patient's dental visits to complete the course of tooth inlay treatment.

The 3-D occlusal profile measuring technique nowadays mainly adopts the following two approaches, including: direct measuring within the mouth cavity, and plaster dental cast scanning, involving respective advantages. One of the advantages of direct measurement within the mouth cavity is its high speed with minimum material consumption. However, when precise measurement of 3-D occlusal profile is required to be conducted within a narrow space defined by the mouth cavity, the measurement is greatly affected by the limited space and complex surroundings, such as the saliva secretion of the patient and residual treatment materials, which confine the measurable range to only acquire partial occlusal profile in each scanning operation, and easily causes data errors due to measurement occlusion; meanwhile, the costly price for commercially available measurement system is the major difficulty in promoting such system that accounts for only 1.5% of the current market share. Though various measuring techniques have been developed in the past few years to accommodate the plaster dental cast scanning technique, there still is a need for the research and development of professional plaster dental cast scanning system, which features with integrated scanning functions to provide the 3-D occlusal profile of a full-dental cast in a rapid and precise manner and is capable of generating data fully compatible with conventional CAD/CAM system at a cost that is acceptable by most dental clinics.

The so-called non-contact 3-D occlusal profile measuring technique implies the use of various approaches to generate a light to be projected onto an object surface for acquiring the information characterizing the object surface through appropriate optical path principles and optical sensors, which could be subdivided into an active type and a passive type in accordance with the way that the light source is projected. The active type non-contact 3-D occlusal profile measuring technique is realized by projecting desired structured light patterns, such as a light spot array, sinusoidal periodic waves, optical beams or other meaningful light patterns, toward the object to be measured. Since the changes in the profile curvature or depth along the object surface will deform the structured light patterns projected onto the object surface, it is necessary to acquire the image of said deformed patterns by adopting appropriate measures, and then to reconstruct the 3-D profile data according to the acquired information, through the triangulation or phase shift principle. On the other hand, the passive type non-contact 3-D profile measuring technique is realized by acquiring the information characterizing the object surface under natural lighting through the optical image technique.

The research of non-contact high-speed acquisition of 3-D profile of objects has been widely investigated. However, there is little research literature aiming at the scanning of occlusal profile. Introductions and discussions with respect to the presently available 3-D occlusal profile measurement system, the measuring principles as applied, as well as its limitations as provided as follows to analyze the underlying principles and limitation in applications of the major commercially available 3-D occlusal profile scanners:

(1) Holographic imaging developed by B. Altschuler (1975):

In this system, laser holography is employed to acquire the 3-D occlusal profile and dimensions of a plaster dental cast, with a measurement resolution reaching 10 microns. This system uses two laser sources, each generating dot and line patterns (Raster patterns). Two raster patterns overlapping each other in a perpendicular manner cause interference. The 3-D data of the object are thus acquired from the changes in the phase of the interferences. However, the high cost of the equipment prevents from subsequent development and actual commercialization.

(2) The Duret/Hennson/Sopha system (1988):

Durent's method is based on the principle of laser holography, which is similar to Altschuler's method. Durent's method primarily made improvements in performing separate regional measurement at various viewing angles aiming at occlusion regions and acquiring 3-D dental cast data by overlapping the 3-D images.

(3) Method Rekow/Erdman-"Minnesota" system (1988):

Developed by Dr. Rekow in the University of Minnesota by utilizing stereo cameras to directly measure the 3-D occlusal profile from the mouth cavity, the primary techniques involved in this method reside in the precise calculation of the 3-D occlusal profile and dimensions based the acquired two dimensional high-resolution image sets. Meanwhile, another character of this system is to develop one occlusal profile database to support the establishment of a full-occlusal profile by computer aided design (CAD) thereby ensuring complete construction of the 3-D occlusal profile. However, since there still remain many problems to be resolved by the 3D stereo detection with respect to the precise measurements of occlusion regions, this system is not presently practicable.

(4) The Procera system (1994):

This system utilizes a mechanical, analog probe to continuously perform contact type measurements of the 3-D occlusal profile and dimensions of a plaster dental cast. The major advantage of said system is the high digitizing accuracy which is within 1-2 microns; however, the contact type measurement resulting in measuring efficiency that is far less than other non-contact type methods, and becomes a major limitation for such system.

(5) The Microdenta system (1995):

This method performs 3-D scanning of a plaster dental cast by utilizing the 3-D linear laser scanning method and an X-Y positioning platform. Such a method significantly improves efficiency of measurements than as to a contact type probe; however, the digitizing accuracy of the measurements is easily influenced by many factors, such as occlusion regions and measurement surfaces due to the congenital limitation of laser measurement, which could not guarantee the general accuracy of the measurements to be within a certain range.

(6) The Computer-Aided Prosthetic system, CAP (1991):

This system utilizes a single-point laser probe to perform the 3-D measurements of a plaster dental cast in cooperation with a two-axis dental cast rotating positioner. The advantages of said system reside in the enhanced digitizing accuracy of the measurements because of the scanning flexibility provided by the single-point laser as well as the positioner, to eliminate the occurrences of the occlusion regions during the measurements; however, the drawback and the primary limitation for such system is slow measurement that takes about thirty minutes in comparison with the use of a linear laser.

(7) The Showa/Nissan CAD/ACM system (1995):

This system performs 3-D measurements at different viewing angles by utilizing a Laser probe and a two-axis dental cast positioner, which significantly enhance the measuring efficiency. Another advantage of this system is the use of a common chamber for cutting of the mouthpiece and the measurement of the dental cast to effectively reduce the equipment cost of the system.

(8) The CEREC Method (1996):

This system is widely used in today's market. Along with the system development, two major ways have been developed for the 3-D measurements of an occlusal profile for ceramic reconstructions, which are (1) plaster dental cast scanning, and (2) intra-oral type dental cast scanning:

(8.1) The plaster dental cast scanning system: the principle involved in taking measurements for this system is very similar to the CAP system, with the measuring time at about thirty minutes for every two teeth and the range of measurements is within the width of two teeth, so as to increase the time for full-range dental cast measurements considerably and becomes a limitation in applications.

(8.2) CEREC system (disclosed in U.S. Pat. No. 6,263, 234) is one of the few measurement systems that could be used to perform 3-D dental scanning inside the mouth cavity. This system projects a grid structured light of infrared (an invisible light) onto the dental occlusal profile inside the cavity. The camera of the system captures images every ¼ interval within four grid movements to acquire the relationship between the depth of the object to be measured and the amount of deformation of the grid pattern (in parallel stripes) to calculate the phase shifting differences for calculation of 3-D dimensions. Since the projected stripes of this system are fixed, the digitizing accuracy and the range of measurement may not be unsatisfactory due to difficulties in measuring occlusal profile with steep stepped surfaces.

The following conclusions could be reached from of detailed investigation of the above-mentioned scanning systems and principles of measurement. That is, in terms of the degree of digitizing accuracy and degree of reliability, the active light used in a non-contact type measurement is more feasible as compared to other means such as passive detection methods. In term of the scanning digitizing accuracy, the measuring principle and strategy adopted in measuring the occluded surfaces (generally directed to the regions that cannot be easily measured) of the occlusal profile are the key factors for acquiring precise measurements. Although many types of 3-D laser measurement probes have been commercialized in the market in recent years, which are widely used in reverse engineering, such measurement system could not provide direct and effective measuring functions for the particular and complex free surfaces of 3-D occlusal profiles.

SUMMARY OF THE INVENTION

In view of the above, this invention provides a 3-D occlusal profile scanner, which mainly utilizes a linear laser structured light projection device and adopts the principle of the triangulation to design a 3-D occlusal profile scanning and measurement system. Besides, the measurement system of this invention could be applied to rapid and precise measurements of a plaster dental cast, and could output the 3-D occlusal profile dimensions of the dental cast to be measured, which is a professional tool for taking measurements of a 3-D plaster dental cast.

It is thus a primary objective of this invention to provide a scanner for scanning the 3-D occlusal profile of a dental cast, including a measurement apparatus which comprises optical projection units and plural image capturing units each including optical components and optical lens. A linear structured light pattern with vertical symmetry is generated by two vertically symmetric semiconductor laser devices, a semi-cylindrical prism and a collimating lens, and projected onto a surface of a dental cast to be measured. Three sets of optical object lenses and image sensing devices placed at different viewing angles are used to capture the images of the complete, deformed structured light pattern. The 3-D occlusal profile dimensions of the dental cast to be measured is then calculated through the triangulation principle.

It is another objective of this invention to provide a method of scanning a 3-D free-form surface to be applied in the rapid and precise profile measurements of a plaster dental cast.

To achieve the above-mentioned objects, this invention discloses a 3-D occlusal profile scanner comprising:

an optical projection unit, including a set of optical lenses and He—Ne semiconductor laser devices for generating a light source by means of two vertically symmetrical semiconductor lasers arranged at suitable orientation of inclination, wherein the light source generates a structured light pattern after passing through the optical lenses, wherein the structured light pattern is subsequently projected onto an object to be measured through the optical lenses;

an image capturing unit, including three sets of optical lenses and image sensing devices situated at various positions for acquiring images of a deformed structured light pattern representing the occlusal profile to be measured, wherein the image sensing devices output information representing the images to a main control unit;

a precision rotating platform unit, including a precision rotating platform and a dental cast vise, wherein the precision rotating platform unit is able to precisely rotate the object to be measured to various measuring orientations for thorough scanning of the 3-D occlusal profile of a single tooth; and a main control unit, connected to the optical projection unit and the image capturing unit, for modulating the structured light pattern output by the optical projection unit and processing the image information acquired by the image capturing unit.

Further disclosed is a method of scanning a miniature 3-D occlusal profile, comprising the steps of:

projecting a structured light pattern onto a dental cast to be measured at a specifically desired orientation, the structured light pattern light source being formed by passing a light source generated by semiconductor lasers through optical lens sets, to ensure ideal projections by the structured light pattern onto essential portions of the dental cast, such as the occlusal surface, the middle proximal surface and the distal surface for dental restoration;

capturing images of a deformed structured light pattern from the object to be measured by three sets of specially designed image capture devices, integrating the images captured by the image capturing devices taken from different viewing angles and acquiring the images representing a complete profile of the object to be measured, wherein the image sensing device outputs information representing the images to a main control unit; and scanning the 3-D occlusal profile, by fixing the dental cast to be measured to an electromotive precision rotating platform by a vise and capturing images by an image capturing unit, wherein a structured light pattern representing a compete cross-section may be generated at the same time so that the dental cast scanning is completed upon rotation of the dental cast for 180 degrees.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF PREFERRED EMBODIMENTS

Figure 1:
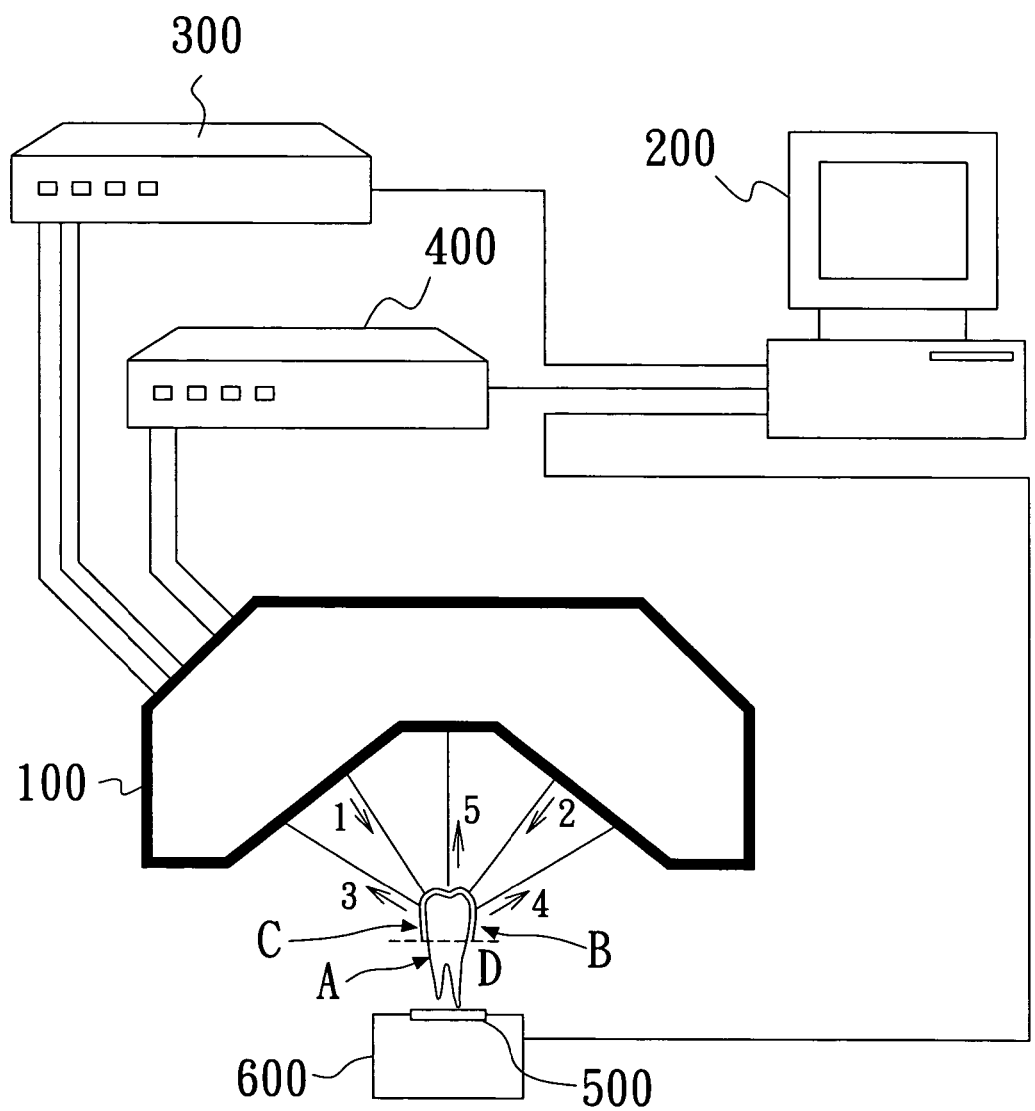
FIG. 1 is schematic view showing a preferred embodiment of the device of this invention.

FIG. 1 illustrates a preferred embodiment for an apparatus for rapid and precise scanning of the occlusal profile of a dental cast according to this invention, comprising, a probe body 100 (shown in FIG. 2) and a main control and calculation unit 200. The probe body 100 is provided therein with optical devices and optical lenses related to optical projection and image capturing. Besides, this invention could be connected to a high speed image processor 300 for processing and storing images, a light intensity controller 400 for controlling intensity of a light source, a dental cast vise 500 for fixing a dental cast, and an electromotive precision rotating platform 600 for rotating and scanning the dental cast.

Among the available optical system of the probe body 100, this embodiment employs two structured light projection units 10 and 20 situated on the sides. Each of the structured light projection units includes a structured light source 1 and 2 that project a linear structured light pattern onto a 3-D dental cast to be measured at a suitable orientation. The two structured light projection units have been precisely calibrated, such that two laser planes are oriented on the same projecting cross section, a bottom surface D of an artificial tooth serves as a datum, a right-side, intermediate and a left-side image capturing units 30, 40 and 50 receive reflected lift-side, intermediate and right-side light beams 4, 5, and 3, respectively, whereby deformed structured light patterns (B and C) at opposing sides of the dental cast engage and align with each other. As such, the occlusal profile sited on the same projection cross-section is completely projected by the structured light at the same time to generate a linear and deformed structured light pattern. Hence, the 3-D (plaster) dental cast A to be measured may be fixed by the dental cast vise 500 and placed on the electromotive precision rotating platform 600 so that the 3-D dental cast scanning may be completed upon rotation of the dental cast for 180 degrees.

The right-side structured light projection unit 10 includes a He—Ne semiconductor laser 11 for generating a projection light source. The point light source is reflected to become a line-type light source by a semi-cylindrical prism 12. A subsequent linear polarizer 13 modulates the intensity and width of the linear light source to enhance its spatial resolution. The linear light source is then aligned by a collimating lens 14 prior to be being projected onto the 3-D plaster dental cast A. Meanwhile, the light intensity controller 400 is applied to adjust the intensity of the light source to obtain a structured light source with fine spatial resolution. The principle for constructing the left-side structured light projection unit 20 is the same as that for the right-side structure light projection unit 10. That is, the left-side structured light projection unit 20 also comprises a He—Ne semiconductor laser 21, a semi-cylindrical prism 22, a linear polarizer 23 and a collimating lens 24.

Figure 2:
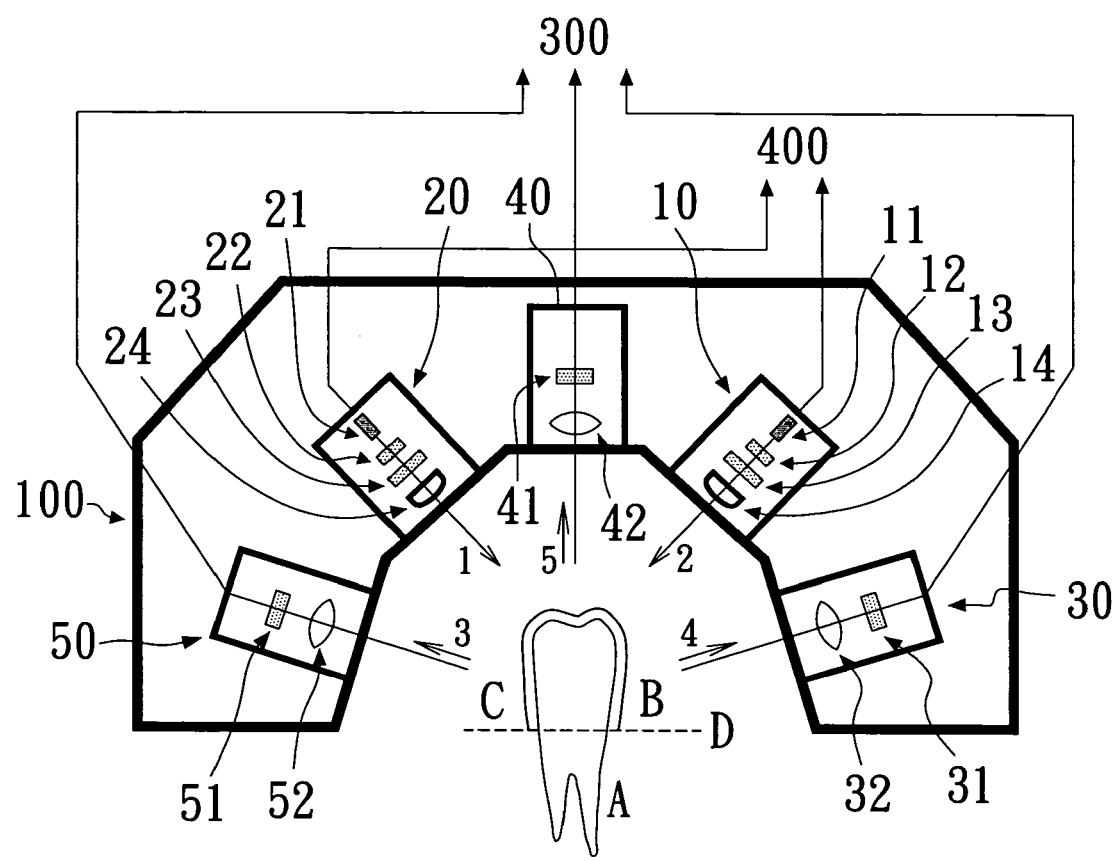
FIG. 2 is an enlarged view showing the measuring probe body of this invention.

To ensure precise and complete acquisition of the linear deformed structured pattern representing the dental cast to be measured, three sets of image capturing unit 30, 40 and 50 are placed at the right side, above, and at the left side of the dental cast to be measured, respectively, as shown in FIG. 2, such that ideal measurements of the essential geometrical surfaces of the dental cast to be measured, such as the occlusal surface, the middle proximal surface and the distal surface, could all be obtained.

The image capturing unit 30 includes an optical focusing lens 32 for focusing the image representing the deformed structure light pattern onto an image sensing unit or device 31, which may be a Charge Coupled Device (CCD). The principle for constructing the intermediate image capturing unit 40 and the left-side image capturing unit 50 is the same as that for the right-side image capturing unit 30, wherein each of the image capturing units is provided therein with an optical focusing lens 42, 52 for forming focused images on an image capturing unit 41, 51. The images are captured and processed by the main control and calculation unit 200 and the high-speed image processor 300.

In summary, this invention integrates the optical projection units and image capturing units into a probe body, and projects the structured light (a linear light pattern produced by projecting a semiconductor laser through an optical lens to serve as measuring means) onto an object to be measured at a desired orientation; plural capturing units are implemented to capture comprehensive information representing the 3-D occlusal profile, based on which information the 3-D occlusal profile is calculated through the triangulation principle, thereby allowing efficient and precise measurement of the 3-D occlusal profile of the plaster dental cast. As compared to conventional 3-D occlusal profile scanner, this invention is featured with improved digitizing accuracy and efficiency.

The present invention has been described with a preferred embodiment thereof and it is understood that the scope and the spirit of the invention as defined by the appended claims.

What is claimed is:

1. An apparatus for rapid and precise scanning of a three-dimensional (3-D) occlusal profile of a dental cast, comprising:
    optical projection units, each including an optical component set and including semiconductor laser devices for generating a light source by means of two vertically symmetrical semiconductor laser diodes arranged at suitable orientation of inclination, wherein the light source generates a structured light pattern after passing through optical lenses of the optical component set, wherein the structured light pattern is subsequently projected onto an object to be measured through the optical lenses of the optical component set;
    image capturing units, including three sets of optical lenses and image sensing devices situated at various positions for acquiring images of a deformed structured light pattern representing the occlusal profile to be measured, wherein the image sensing devices output information representing the images to a main control unit;
    a precision rotating platform unit, including a precision rotating platform and a dental cast vise, wherein the precision rotating platform unit is able to precisely rotate the object to be measured to various measuring orientations for complete scanning of the 3-D occlusal profile of a single tooth; and
    the main control unit, connected to the optical projection units and the image capturing units, for modulating the structured light pattern output by the optical projection unit and processing the image information acquired by the image capturing unit.

2. The apparatus of claim 1, further comprising a high-speed image processor for capturing and processing the images.

3. The apparatus of claim 1, further comprising a light intensity controller for controlling intensity of the light source and enhancing spatial resolution of the structured light source.

4. The apparatus of claim 1, wherein the image sensing devices of the image capturing units are each a charge-coupled device (CCD).

5. The apparatus of claim 1, wherein each optical component set of the optical projection units comprises a collimating lens, a linear polarizer, and a semi-cylindrical prism.

6. The apparatus of claim 5, wherein an incidence light source of the optical projection units is each generated by a He—Ne semiconductor laser and sequentially passes through the semi-cylindrical prism, linear polarizer and collimating lens.

7. The apparatus of claim 1, wherein the image information acquired by the image capturing units is formed by optical focusing lenses and the image sensing devices.

8. A method for rapid and precise scanning of a three-dimensional (3-D) profile of a dental cast, comprising the steps of:
    projecting a structured light pattern onto a dental cast to be measured at a specifically desired orientation, the structured light pattern being formed by passing a light source generated by semiconductor lasers through optical lens sets, to ensure ideal projections by the structured light pattern onto an entirety of the dental cast;
    capturing images of a deformed structured light pattern from the object to be measured by image capturing units comprising three sets of specially designed image capture devices, integrating the images captured by the image capturing devices taken from different viewing angles and projecting the images representing a complete profile of the object to be measured to image sensing devices;
    scanning a 3-D occlusal profile, by fixing the dental cast to be measured to an electromotive precision rotating platform by a vise and capturing images by the image capturing units, wherein a structured light pattern representing a complete cross-section of the measured object may be generated at the same time so that the dental cast scanning is completed upon rotation of the dental cast for 180 degrees;
    transmitting stored image information of the images captured by the image capturing devices to the main control unit; and
    calculating precise measurements of the 3-D occlusal profile of the dental cast such that a digitizing accurate 3-D occlusal profile of the dental cast is obtained.

9. The method of claim 8, wherein the images are rapidly captured and processed by a high-speed image processor.

10. The method of claim 8, wherein the main control unit performs the steps of:
    generating the structured light pattern by modulating the structured light to control the adequate intensity of the structured light pattern with high spatial resolution; and
    processing the images by controlling the image capturing, processing the images and calculating the 3-D occlusal profile.

11. The method of claim 10, wherein the step of processing the images employs triangulation to calculate the 3-D occlusal profile of the object to be measured.

* * * * *